(12) United States Patent
Schlebusch et al.

(10) Patent No.: US 12,310,708 B2
(45) Date of Patent: May 27, 2025

(54) SYSTEMS AND METHODS FOR DETERMINING A FLOW SPEED OF A FLUID FLOWING THROUGH A CARDIAC ASSIST DEVICE

(71) Applicant: KARDION GMBH, Stuttgart (DE)

(72) Inventors: Thomas Alexander Schlebusch, Renningen (DE); Tobias Schmid, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 1112 days.

(21) Appl. No.: 15/734,523

(22) PCT Filed: Jun. 6, 2019

(86) PCT No.: PCT/EP2019/064807
§ 371 (c)(1),
(2) Date: Oct. 15, 2021

(87) PCT Pub. No.: WO2019/234166
PCT Pub. Date: Dec. 12, 2019

(65) Prior Publication Data
US 2022/0039669 A1 Feb. 10, 2022

(30) Foreign Application Priority Data

Jun. 6, 2018 (DE) .......................... 102018208933.7

(51) Int. Cl.
*A61B 5/029* (2006.01)
*A61B 5/00* (2006.01)
(Continued)

(52) U.S. Cl.
CPC .............. *A61B 5/029* (2013.01); *A61B 5/686* (2013.01); *A61B 5/6869* (2013.01); *A61B 8/065* (2013.01);
(Continued)

(58) Field of Classification Search
CPC ....... A61B 5/029; A61B 5/686; A61B 5/6869; A61B 8/065; A61B 8/488; A61B 8/0883;
(Continued)

(56) References Cited

U.S. PATENT DOCUMENTS

| 3,088,323 A | 5/1963 | Welkowitz et al. |
| 4,023,562 A | 5/1977 | Hynecek et al. |

(Continued)

FOREIGN PATENT DOCUMENTS

| CA | 3 122 415 | 7/2020 |
| CN | 1192351 A | 9/1998 |

(Continued)

OTHER PUBLICATIONS

Vollkron et al., "Advanced Suction Detection for an Axial Flow Pump", Artificial Organs, 2006, vol. 30, No. 9, pp. 665-670.

(Continued)

*Primary Examiner* — Mark W. Bockelman
(74) *Attorney, Agent, or Firm* — Knobbe, Martens, Olson & Bear, LLP (57) ABSTRACT

The invention relates to a method for determining at least a flow velocity or a fluid volume flow (5) of a fluid flowing through an implanted vascular support system (1), comprising the following steps: a) carrying out a pulsed Doppler measurement by means of an ultrasonic sensor (2) of the support system (1), b) evaluating a measurement result from step a), which has a possible ambiguity, c) providing at least one operating parameter of a flow machine (3) of the support system (1), d) determining at least the flow velocity or the fluid volume flow (5) using the measurement result evaluated in step b), wherein the possible ambiguity of the measurement result is corrected using the operating parameter.

16 Claims, 5 Drawing Sheets (51) Int. Cl.
*A61B 8/00* (2006.01)
*A61B 8/06* (2006.01)
*A61M 60/178* (2021.01)
*A61M 60/226* (2021.01)
*A61M 60/237* (2021.01)
*A61M 60/523* (2021.01)

(52) U.S. Cl.
CPC ............ *A61B 8/488* (2013.01); *A61M 60/178* (2021.01); *A61M 60/226* (2021.01); *A61M 60/237* (2021.01); *A61M 60/523* (2021.01); *A61M 2205/3334* (2013.01); *A61M 2205/3375* (2013.01)

(58) Field of Classification Search
CPC ............ A61B 8/0891; A61B 8/06; A61B 8/12; A61M 60/178; A61M 60/226; A61M 60/237; A61M 60/523; A61M 2205/3334; A61M 2205/3375; A61M 60/13; A61M 2230/04; A61M 60/816; A61M 60/857
See application file for complete search history.

(56) References Cited

U.S. PATENT DOCUMENTS

| | | | |
|---|---|---|---|
| 4,559,952 A | 12/1985 | Angelsen et al. | |
| 4,680,730 A * | 7/1987 | Omoda | G06F 15/8084 711/149 |
| 4,781,525 A | 11/1988 | Hubbard et al. | |
| 4,888,011 A | 12/1989 | Kung et al. | |
| 4,889,131 A | 12/1989 | Salem et al. | |
| 4,902,272 A | 2/1990 | Milder et al. | |
| 5,045,051 A | 9/1991 | Milder et al. | |
| 5,269,811 A | 12/1993 | Hayes | |
| 5,289,821 A | 3/1994 | Swartz | |
| 5,456,715 A | 10/1995 | Liotta | |
| 5,527,159 A | 6/1996 | Bozeman, Jr. et al. | |
| 5,581,038 A | 12/1996 | Lampropoulos | |
| 5,613,935 A | 3/1997 | Jarvik | |
| 5,662,115 A | 9/1997 | Torp | |
| 5,676,651 A | 10/1997 | Larson, Jr. et al. | |
| 5,720,771 A | 2/1998 | Snell | |
| 5,752,976 A | 5/1998 | Duffin et al. | |
| 5,766,207 A | 6/1998 | Potter et al. | |
| 5,827,203 A | 10/1998 | Nita | |
| 5,865,759 A | 2/1999 | Koblanski | |
| 5,888,242 A | 3/1999 | Antaki et al. | |
| 5,904,708 A | 5/1999 | Goedeke | |
| 5,911,685 A | 6/1999 | Siess et al. | |
| 5,964,694 A | 10/1999 | Siess et al. | |
| 5,980,465 A | 11/1999 | Elgas | |
| 6,007,478 A | 12/1999 | Siess et al. | |
| 6,024,704 A | 2/2000 | Meador et al. | |
| 6,053,873 A | 4/2000 | Govari et al. | |
| 6,167,765 B1 * | 1/2001 | Weitzel | A61M 1/3658 73/861.18 |
| 6,176,822 B1 | 1/2001 | Nix et al. | |
| 6,183,412 B1 | 2/2001 | Benkowsi et al. | |
| 6,185,460 B1 | 2/2001 | Thompson | |
| 6,190,324 B1 | 2/2001 | Kieval et al. | |
| 6,210,318 B1 | 4/2001 | Lederman | |
| 6,231,498 B1 | 5/2001 | Pfeiffer et al. | |
| 6,245,007 B1 | 6/2001 | Bedingham et al. | |
| 6,314,322 B1 | 11/2001 | Rosenberg | |
| 6,351,048 B1 | 2/2002 | Schob et al. | |
| 6,398,734 B1 | 6/2002 | Cimochowski et al. | |
| 6,432,136 B1 | 8/2002 | Weiss et al. | |
| 6,438,409 B1 | 8/2002 | Malik et al. | |
| 6,512,949 B1 | 1/2003 | Combs et al. | |
| 6,530,876 B1 | 3/2003 | Spence | |
| 6,540,658 B1 | 4/2003 | Fasciano et al. | |
| 6,540,659 B1 | 4/2003 | Milbocker | |
| 6,561,975 B1 | 5/2003 | Pool et al. | |
| 6,579,257 B1 | 6/2003 | Elgas et al. | |
| 6,602,182 B1 | 8/2003 | Milbocker | |
| 6,605,032 B2 | 8/2003 | Benkowsi et al. | |
| 6,652,447 B2 | 11/2003 | Benkowsi et al. | |
| 6,731,976 B2 | 5/2004 | Penn et al. | |
| 6,879,126 B2 | 4/2005 | Paden et al. | |
| 6,912,423 B2 | 6/2005 | Ley et al. | |
| 6,949,066 B2 | 9/2005 | Bearnson et al. | |
| 6,984,201 B2 | 1/2006 | Khaghani et al. | |
| 7,010,954 B2 | 3/2006 | Siess | |
| 7,022,100 B1 | 4/2006 | Aboul-Hosn et al. | |
| 7,024,244 B2 | 4/2006 | Muhlenberg et al. | |
| 7,070,555 B2 | 7/2006 | Siess | |
| 7,083,588 B1 | 8/2006 | Shmulewitz et al. | |
| 7,138,776 B1 | 11/2006 | Gauthier et al. | |
| 7,160,243 B2 | 1/2007 | Medvedev | |
| 7,175,588 B2 | 2/2007 | Morello | |
| 7,177,681 B2 | 2/2007 | Xhu | |
| 7,238,151 B2 | 7/2007 | Frazier | |
| 7,396,327 B2 | 7/2008 | Morello | |
| 7,513,864 B2 | 4/2009 | Kantrowitz et al. | |
| 7,520,850 B2 | 4/2009 | Brockway | |
| 7,527,599 B2 | 5/2009 | Hickey | |
| 7,591,777 B2 | 9/2009 | LaRose | |
| 7,744,560 B2 | 6/2010 | Struble | |
| 7,794,384 B2 | 9/2010 | Sugiura et al. | |
| 7,819,916 B2 | 10/2010 | Yaegashi | |
| 7,850,593 B2 | 12/2010 | Vincent et al. | |
| 7,850,594 B2 | 12/2010 | Sutton et al. | |
| 7,856,335 B2 | 12/2010 | Morello et al. | |
| 7,862,501 B2 | 1/2011 | Woodward et al. | |
| 7,951,062 B2 | 5/2011 | Morello | |
| 7,951,129 B2 | 5/2011 | Chinchoy | |
| 7,963,905 B2 | 6/2011 | Salmonsen et al. | |
| 7,988,728 B2 | 8/2011 | Ayre | |
| 8,075,472 B2 | 12/2011 | Zilbershlag et al. | |
| 8,190,390 B2 | 5/2012 | Morello et al. | |
| 8,211,028 B2 | 7/2012 | Karamanoglu et al. | |
| 8,303,482 B2 | 11/2012 | Schima et al. | |
| 8,323,173 B2 | 12/2012 | Benkowsi et al. | |
| 8,435,182 B1 | 5/2013 | Tamura | |
| 8,449,444 B2 | 5/2013 | Poirier | |
| 8,545,380 B2 | 10/2013 | Farnan et al. | |
| 8,585,572 B2 | 11/2013 | Mehmanesh | |
| 8,591,393 B2 | 11/2013 | Walters et al. | |
| 8,594,790 B2 | 11/2013 | Kjellstrom et al. | |
| 8,622,949 B2 | 1/2014 | Zafirelis et al. | |
| 8,657,733 B2 | 2/2014 | Ayre et al. | |
| 8,657,875 B2 | 2/2014 | Kung et al. | |
| 8,715,151 B2 | 5/2014 | Poirier | |
| 8,747,293 B2 | 6/2014 | Arndt et al. | |
| 8,849,398 B2 | 9/2014 | Evans | |
| 8,864,643 B2 | 10/2014 | Reichenbach et al. | |
| 8,864,644 B2 | 10/2014 | Yomtov | |
| 8,876,685 B2 | 11/2014 | Crosby et al. | |
| 8,882,477 B2 | 11/2014 | Fritz, IV et al. | |
| 8,888,728 B2 | 11/2014 | Aboul-Hosn et al. | |
| 8,897,873 B2 | 11/2014 | Schima et al. | |
| 8,903,492 B2 | 12/2014 | Soykan et al. | |
| 9,091,271 B2 | 7/2015 | Bourque | |
| 9,297,735 B2 | 3/2016 | Graichen et al. | |
| 9,308,305 B2 | 4/2016 | Chen et al. | |
| 9,345,824 B2 | 5/2016 | Mohl et al. | |
| 9,371,826 B2 | 6/2016 | Yanai et al. | |
| 9,427,508 B2 | 8/2016 | Reyes et al. | |
| 9,474,840 B2 | 10/2016 | Siess | |
| 9,492,601 B2 | 11/2016 | Casas et al. | |
| 9,511,179 B2 | 12/2016 | Casas et al. | |
| 9,555,173 B2 | 1/2017 | Spanier | |
| 9,555,175 B2 | 1/2017 | Bulent et al. | |
| 9,556,873 B2 | 1/2017 | Yanai et al. | |
| 9,566,374 B2 | 2/2017 | Spence et al. | |
| 9,636,442 B2 | 5/2017 | Karmon et al. | |
| 9,656,010 B2 | 5/2017 | Burke | |
| 9,669,142 B2 | 6/2017 | Spanier et al. | |
| 9,669,144 B2 | 6/2017 | Spanier et al. | |
| 9,694,123 B2 | 7/2017 | Bourque et al. | |
| 9,713,701 B2 | 7/2017 | Sarkar et al. | |
| 9,744,282 B2 | 8/2017 | Rosenberg et al. | |
| 9,789,236 B2 | 10/2017 | Bonde | |

(56) References Cited

U.S. PATENT DOCUMENTS

| | | |
|---|---|---|
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |
| 9,943,236 B2 | 4/2018 | Bennett et al. |
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 10,864,308 B2 | 12/2020 | Muller et al. |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 12,059,559 B2 | 8/2024 | Muller et al. |
| D1,043,730 S | 9/2024 | Lussier et al. |
| D1,043,731 S | 9/2024 | Lussier et al. |
| 12,076,544 B2 | 9/2024 | Siess et al. |
| 12,097,016 B2 | 9/2024 | Goldvasser |

(56) References Cited

U.S. PATENT DOCUMENTS

| | | |
|---|---|---|
| 12,102,815 B2 | 10/2024 | Dhaliwal et al. |
| 12,144,650 B2 | 11/2024 | Spanier et al. |
| 12,144,976 B2 | 11/2024 | Baumbach et al. |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0022785 A1 | 2/2002 | Romano |
| 2002/0082585 A1 | 6/2002 | Carroll et al. |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2003/0199727 A1 | 10/2003 | Burke |
| 2004/0022640 A1 | 2/2004 | Siess et al. |
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0108901 A1 | 5/2006 | Mao-Chin |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0069354 A1 | 3/2007 | Dangelmaier |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0172505 A1 | 7/2011 | Kim |
| 2011/0184301 A1 | 7/2011 | Holmstrom |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0203476 A1 | 8/2012 | Dam |
| 2012/0245404 A1 | 9/2012 | Smith |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0072846 A1 | 3/2013 | Heide et al. |
| 2013/0116575 A1 | 5/2013 | Mickle et al. |
| 2013/0144379 A1 | 6/2013 | Najafi et al. |
| 2013/0289334 A1 | 10/2013 | Badstibner |
| 2013/0289376 A1 | 10/2013 | Lang |
| 2013/0303831 A1 | 11/2013 | Evans |
| 2013/0304404 A1 | 11/2013 | Dam |
| 2014/0005467 A1 | 1/2014 | Farnan et al. |
| 2014/0013852 A1 | 1/2014 | Brown et al. |
| 2014/0030122 A1 | 1/2014 | Ozaki |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0275727 A1 | 9/2014 | Bonde |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decré et al. |
| 2016/0151553 A1 | 6/2016 | Bonde |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1 | 9/2016 | Panescu |
| 2016/0302672 A1 | 10/2016 | Kuri |
| 2016/0317043 A1 | 11/2016 | Campo |
| 2016/0338629 A1 | 11/2016 | Doerr |
| 2017/0010144 A1 | 1/2017 | Lenner et al. |
| 2017/0021070 A1 | 1/2017 | Petersen |

(56) References Cited

U.S. PATENT DOCUMENTS

| | | |
|---|---|---|
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0348470 A1 | 12/2017 | D'Ambrosio et al. |
| 2017/0354812 A1 | 12/2017 | Callaghan et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0110910 A1 | 4/2018 | Rodemerk et al. |
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0316209 A1 | 11/2018 | Gliner |
| 2018/0326131 A1 | 11/2018 | Muller et al. |
| 2018/0333059 A1 | 11/2018 | Casas |
| 2018/0353667 A1 | 12/2018 | Moyer et al. |
| 2018/0369469 A1 | 12/2018 | Le Duc De Lillers et al. |
| 2019/0001038 A1 | 1/2019 | Yomtov et al. |
| 2019/0054223 A1 | 2/2019 | Frazier et al. |
| 2019/0083690 A1 | 3/2019 | Siess et al. |
| 2019/0192752 A1 | 6/2019 | Tiller et al. |
| 2019/0192753 A1 | 6/2019 | Liu et al. |
| 2019/0209755 A1 | 7/2019 | Nix et al. |
| 2019/0209758 A1 | 7/2019 | Tuval et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0282741 A1 | 9/2019 | Franano et al. |
| 2019/0282744 A1 | 9/2019 | D'Ambrosio et al. |
| 2019/0351117 A1 | 11/2019 | Cambronne et al. |
| 2019/0351118 A1 | 11/2019 | Graichen et al. |
| 2020/0016309 A1 | 1/2020 | Kallenbach et al. |
| 2020/0038567 A1 | 2/2020 | Siess et al. |
| 2020/0060559 A1 | 2/2020 | Edelman et al. |
| 2020/0069857 A1 | 3/2020 | Schwammenthal et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2021/0268264 A1 | 9/2021 | Stotz |
| 2021/0290087 A1 | 9/2021 | Schlebusch |
| 2021/0290930 A1 | 9/2021 | Kasel |
| 2021/0290933 A1 | 9/2021 | Stotz |
| 2021/0339002 A1 | 11/2021 | Schlebusch et al. |
| 2021/0339004 A1 | 11/2021 | Schlebusch et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346677 A1 | 11/2021 | Baumbach et al. |
| 2021/0346678 A1 | 11/2021 | Baumbach et al. |
| 2021/0378523 A1 | 12/2021 | Budde |
| 2021/0379359 A1 | 12/2021 | Schellenberg |
| 2021/0379360 A1 | 12/2021 | Schellenberg |
| 2021/0393944 A1 | 12/2021 | Wenning |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0047173 A1 | 2/2022 | Stotz et al. |
| 2022/0050037 A1 | 2/2022 | Stotz et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0105339 A1 | 4/2022 | Nix et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161019 A1 | 5/2022 | Mitze et al. |
| 2022/0361762 A1 | 11/2022 | Lalancette |
| 2023/0173250 A1 | 6/2023 | Stigloher |
| 2023/0191141 A1 | 6/2023 | Wenning et al. |
| 2024/0011808 A1 | 1/2024 | Winzer et al. |
| 2024/0074828 A1 | 3/2024 | Wenning |
| 2024/0245902 A1 | 7/2024 | Schlebusch et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |

(56) References Cited

FOREIGN PATENT DOCUMENTS

| | | |
|---|---|---|
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 4 034 221 | 11/2024 |
| EP | 3 809 960 | 12/2024 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |

(56) References Cited

FOREIGN PATENT DOCUMENTS

| | | |
|---|---|---|
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/005228 | 1/2018 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

Vollkron et al., "Development of a Suction Detection System for Axial Blood Pumps", Artificial Organs, 2004, vol. 28, No. 8, pp. 709-716.

Atkinson et al., "Pulse-Doppler Ultrasound and Its Clinical Application", The Yale Journal of Biology and Medicine, 1977, vol. 50, pp. 367-373.
Leguy et al., "Assessment of Blood Volume Flow in Slightly Curved Arteries from a Single Velocity Profile", Journal of Biomechanics, 2009, pp. 1664-1672.
Lombardi et al., "Flow Rate Profiler: an instrument to measure blood velocity profiles", Ultrasonics, 2001, vol. 39, pp. 143-150.
Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
"Understanding Hot-Wire Anemometry", Advanced Thermal Solutions, Inc., 2007, pp. 13-17.
Vieli, A., "Doppler Flow Determination", BJA: British Journal of Anaesthesia, 1988, vol. 60, pp. 107S-112S.
Yuanyuan et al., "Characteristics Analysis for Doppler Ultrasound Blood Flow Signals", China Medical Device Information, 5(1), Feb. 28, 1999, pp. 36-42.
Zhang, Dabiao et al., "Design of Microwave Velocity and Distance Monitor System", Instrument Technique and Sensor, Hebei Normal University, Apr. 25, 2004, pp. 3.
Hertz Ph.D. et al, "Ultrasonic Engineering in Heart Diagnosis", The American Journal of Cardiology, Jan. 1967, vol. 19, No. 1, pp. 6-17.
International Preliminary Report on Patentability and Written Opinion received in PCT Application No. PCT/EP2019/064807, dated Dec. 17, 2020 in 16 pages.
International Search Report and Written Opinion received in PCT Application No. PCT/EP2019/064807, dated Oct. 17, 2019 in 21 pages.
Kong et al., "A Stein Equation Approach for Solutions to the Diophantine Equations," 2010 Chinese Control and Decision Conference, Xuzhou, May 26, 2010, pp. 3024-3028.
Koseli et al., "Online Viscosity Measurement of Complex Solutions Using Ultrasound Doppler Velocimetry", Turk J Chem, Jan. 2006, vol. 30, pp. 297-305.
McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.
Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.
Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
HeartMate 3™ Left Ventricular Assist System, Instructions for Use, Thoratec Corporation, Aug. 2017, pp. 536. [Uploaded in 3 parts].

* cited by examiner

SYSTEMS AND METHODS FOR DETERMINING A FLOW SPEED OF A FLUID FLOWING THROUGH A CARDIAC ASSIST DEVICE

BACKGROUND

Field

The invention relates to a method for determining a flow velocity of a fluid flowing through an implanted vascular support system, an implantable vascular support system, and a use of an operating parameter of a flow machine of an implanted vascular support system. The invention is in particular used in (fully) implanted left-heart support systems (LVAD).

Description of the Related Art

It is known to integrate ultrasonic volume flow sensors into heart support systems in order to therewith detect the so-called pump volume flow, which quantifies the fluid volume flow through the support system itself. The ultrasonic volume flow sensors can carry out pulsed Doppler measurements or use the pulsed Doppler (pulsed wave Doppler; in short: PWD) method. This method requires only one ultrasound transducer element and allows precise selection of the distance of the observation window from the ultrasound element.

The task of a cardiac support system is to convey blood. In this case, the so-called heart-time volume (HTV, usually indicated in liters per minute) is highly clinically relevant. In other words, the heart-time volume in this case relates to the total volume flow of blood from a ventricle, in particular from the left ventricle, to the aorta. Correspondingly clear is the attempt to collect this parameter as a measured value during operation of a cardiac support system.

Depending on the level of support, which describes the proportion of volume flow conveyed by a conveying means, such as a pump of the support system, to the total volume flow of blood from the ventricle to the aorta, a certain volume flow reaches the aorta via the physiological path through the aortic valve. The heart-time volume or the total volume flow ($Q_{HTV}$) from the ventricle to the aorta is therefore usually the sum of the pump volume flow ($Q_p$) and the aortic valve volume flow ($Q_a$).

An established method for the determination of the heart-time volume ($Q_{HTV}$) in the clinical setting is the use of dilution methods, which, however, all rely on a catheter inserted transcutaneously and therefore can only provide heart-time volume measurement data during cardiac surgery and during the subsequent stay in intensive care. For high levels of support, $Q_a$ approaches zero so that approximately $Q_p \approx Q_{HZV}$ applies. Accordingly, at least in these cases, the heart-time volume can be determined at least approximately via the pump volume flow. An established method for measuring the pump volume flow ($Q_p$) is the correlation of the operating parameters of the support system, predominantly the electrical power consumption, possibly supplemented by further physiological parameters, such as the blood pressure. Since these methods are based on statistical assumptions and the underlying pump characteristic map of the support system used, the correlated $Q_p$ are error-prone. In order to increase the measurement quality of the parameter $Q_p$, the inclusion of a flow sensor is therefore desirable.

A particularly suitable sensor method for determining flow velocities and thus also volume flows is ultrasound, in particular the pulsed wave Doppler method (PWD) since it requires only one bidirectional ultrasound transducer element and allows precise selection of the distance of the observation window in which the measured values are collected. It is thus possible to carry out the flow velocity measurement in the range in which suitable flow conditions prevail.

In a PWD system, ultrasonic pulses are sent out at a defined pulse repetition rate (PRF). If the flow velocity and flow direction are unknown, the PRF must exceed at least twice the maximum occurring Doppler frequency shift in order to not violate the Nyquist theorem. If this condition is not met, aliasing occurs, i.e., ambiguities in the determined frequency spectrum. When detecting a frequency in the frequency spectrum, it can no longer be unambiguously assigned to one but several flow velocities.

Due to the geometric design of the measurement setup in heart support systems (VAD), the measurement range or the observation window may be so far away from the ultrasound transducer that the signal transit time of the ultrasonic pulse from the transducer to the measurement range and back to the transducer is not negligible. Since a new ultrasonic pulse may only be sent out if the preceding one no longer delivers significant echoes, the signal transit time limits the maximum possible PRF. In the case of the high flow velocities prevailing in heart support systems and the geometric boundary conditions for the distance of the observation window from the ultrasound element, there is inevitably a violation of the Nyquist sampling theorem, which results in ambiguities being produced in the spectrum.

Heart support systems with ultrasonic sensors that do not use the PWD method are usually equipped with two ultrasound transducers so that the described transit time problem can occur but can be solved otherwise with appropriate implementation. However, heart support systems with ultrasonic sensors that use the PWD method are susceptible to the described effect, in particular in the case of moderate to high flow velocities. The current state of the art is the measure to select the defined pulse repetition rate such that aliasing does not occur or to suitably adjust, if possible, both the geometric conditions and the ultrasound frequency.

SUMMARY

The object of the invention is to specify an improved method for determining a flow velocity of a fluid flowing through an implanted vascular support system and to create an improved implantable vascular support system in which the flow velocity of a fluid flowing through it can be determined.

In particular, it is an object of the invention to create a method for determining a flow velocity of a fluid and an improved implantable vascular support system, in which the determination of the flow velocity of a fluid flowing through it is provided, in which the determination of the flow velocity at the flow velocities prevailing in a heart support system is possible with only one ultrasound transducer, even in the case of a long signal transit time of an ultrasonic pulse from the ultrasound transducer to the measurement range and back.

This object is achieved by the systems and methods disclosed herein.

Advantageous embodiments of the invention are specified herein.

In some embodiments, a method for determining at least a flow velocity or a fluid volume flow of a fluid flowing through an implanted vascular support system is proposed here, comprising the following steps:
a) carrying out a pulsed Doppler measurement by means of an ultrasonic sensor of the support system,
b) evaluating a measurement result from step a), which has a possible ambiguity,
c) providing at least one operating parameter of a flow machine of the support system,
d) determining at least the flow velocity or the fluid volume flow using the measurement result evaluated in step b),
wherein the possible ambiguity of the measurement result is corrected using the operating parameter.

The vascular support system is preferably a cardiac support system, particularly preferably a ventricular support system. The support system is regularly used to support the conveyance of blood in the blood circulation of a person, if appropriate patients. The support system can be arranged at least partially in a blood vessel. The blood vessel is, for example, the aorta, in particular in the case of a left-heart support system, or the common trunk (Truncus pulmonalis) into the two pulmonary arteries, in particular in the case of a right-heart support system. The support system is preferably arranged at the exit of the left ventricle of the heart or the left heart chamber. The support system is particularly preferably arranged in the aortic valve position.

The solution proposed here contributes in particular to providing an aliasing compensation method for an ultrasonic volume flow sensor in a heart support system. The method can contribute to determining a fluid flow velocity and/or a fluid volume flow from a ventricle of a heart, in particular from a (left) ventricle of a heart, to the aorta in the region of a (fully) implanted (left) ventricular (heart) support system. The fluid is regularly blood. The flow velocity is determined in a fluid flow or fluid volume flow, which flows through the support system, in particular through an (inlet) tube or an (inlet) cannula of the support system. The method advantageously allows the flow velocity and/or the fluid volume flow of the blood flow to be determined with high quality even outside the surgical scenario, in particular by the implanted support system itself.

The solution proposed here can particularly advantageously use the fact that based on the motor characteristic map, a rough estimation of the pump flow is possible (only) from the rotation rate of the drive or on the basis of the differential pressure across the flow machine and the rotation rate. The in particular rough estimate of the flow rate from the operating parameters of the flow machine is used in particular to resolve the ambiguities in the spectrum and to enable highly precise flow measurement by the ultrasonic sensor.

In step a), a pulsed Doppler measurement is carried out by means of an ultrasonic sensor of the support system. In order to carry out the pulsed Doppler measurement, the pulsed Doppler (pulsed wave Doppler; in short: PWD) method is in particular used. In particular, a PWD measurement cycle is run through in step a).

In step b), a measurement result from step a) which has a possible ambiguity is evaluated. "Possible ambiguity" means in other words in particular that the measurement result or all measurement results do not necessarily always have to have an ambiguity. In particular, in the case of a comparatively high flow velocity, as commonly occurring in the support systems in question here, the measurement result generally has an ambiguity. However, at a comparatively low flow velocity, it can also happen that the measurement result is unambiguous.

The measurement result can furthermore be provided in particular after step b). In this case, the measurement result can, for example, be provided as raw data (e.g., frequency spectrum) or as raw measurement result or as already at least partially preprocessed measurement result (e.g., as a (measured) flow velocity and/or as a (measured) fluid volume flow). The measurement result can be provided to a processing unit of the support system, for example.

In step c), at least one operating parameter of a flow machine of the support system is provided. The operating parameter can be provided to a processing unit of the support system, for example. The measurement result provided in step b) and the operating parameter provided in step c) are generally detected with respect to the same fluid flow, e.g., in the same (temporal and/or spatial) observation window. In other words, this means in particular that the measurement result provided in step b) and the operating parameter provided in step c) relate to substantially the same measurement time or have substantially the same time stamp and/or relate to the same measuring point. In this case, "substantially" in particular describes a deviation of less than one second. A time difference (generally of less than one second) can be taken into account until the operating parameter (or a change thereof) affects the measuring point. This can also be described in such a way that the measurement result provided in step b) and the operating parameter provided in step c) are associated with each other. At least one operating parameter associated with the measurement result provided in step b) is preferably provided in step c).

In step d), the (actual) flow velocity is determined using the measurement result evaluated in step b). If a raw measurement result is evaluated in step b) and then provided, it is particularly advantageous if a (measured) flow velocity is determined therefrom (e.g., in step d). If a pre-processed measurement result for a (measured) flow velocity is provided in step b), it can advantageously be used directly in step d). The (measured) flow velocity is generally not unambiguous. Furthermore, it is advantageous if an estimated flow velocity is determined on the basis of the operating parameter provided in step c). The (actual) flow velocity can now be determined, for example, by selecting the measured flow velocity that is closest to the estimated flow velocity.

Alternatively or cumulatively, an (actual) fluid volume flow (instead of the flow velocity) can be determined in step d). If a raw measurement result is provided in step b), it is particularly advantageous if a (measured) fluid volume flow is determined therefrom. If a pre-processed measurement result for a (measured) fluid volume flow is provided in step b), it can advantageously be used directly in step d). The (measured) fluid volume flow is generally not unambiguous. Furthermore, it is advantageous if an estimated fluid volume flow is determined on the basis of the operating parameter provided in step c). The (actual) flow volume flow can now be determined, for example, by selecting the measured fluid volume flow that is closest to the estimated fluid volume flow.

In the sense of the solution proposed here, the possible ambiguity of the measurement result is corrected or resolved using the operating parameter. The measurement result is generally ambiguous. This ambiguity can be explained in particular by the generally present violation of the Nyquist sampling theorem in this case. This violation of the Nyquist sampling theorem is caused in particular by comparatively long signal transit times existing in the support system between the ultrasonic sensor and the observation window or measurement range and a new ultrasonic pulse in the pulsed Doppler measurements generally being sent out only if the echo of an ultrasonic pulse sent out immediately beforehand was received or has died away.

The possible ambiguity can, for example, be corrected or resolved in step d). In this context, the flow velocity can be determined in step d) using the (possibly ambiguous) measurement result evaluated and/or provided in step b) and the operating parameter provided in step c), wherein the possible ambiguity of the measurement result is corrected using the operating parameter. A possibility to carry out such a correction or to resolve a possible ambiguity has already been described above. By way of example, the measured flow velocity or the measured fluid volume flow that is closest to the estimated flow velocity or the estimated fluid volume flow is selected in this case.

Alternatively, the possible ambiguity can (already) be corrected or resolved in step b), for example. This alternative can also be referred to as a priori estimation or as a priori selection or pre-selection. In other words, this means in particular that the possible ambiguity is already corrected or resolved during the evaluation of the measurement result. This can be particularly advantageous take place such that (only) the range or section of the (raw) measurement result in which a plausible result is to be expected is evaluated. The evaluated (no longer ambiguous) measurement result can in this case be provided in step b). The evaluated (no longer ambiguous) measurement result can in this case be used in step d).

"A priori" here means in particular that the operating parameter is provided and/or the estimated flow velocity or the estimated fluid volume flow is determined before the (possibly ambiguous) measurement result is evaluated (and, if applicable, provided). For example, the operating parameter, the a priori estimated flow velocity and/or the a priori estimated fluid volume flow (possibly in the form of a window function or windowing) can contribute to a pre-selection in order to evaluate and/or provide only a plausible measurement result or only the plausible part of the measurement result. For this purpose, a (reflected and then) received ultrasonic pulse can, for example, only be evaluated in the (frequency) section in which a plausible result is to be expected.

According to an advantageous embodiment, it is proposed that a new ultrasonic pulse is only sent out in step a) if an echo of an ultrasonic pulse sent out immediately beforehand has (sufficiently) died away and/or was received. A new ultrasonic pulse is preferably sent out only if all (significant) echoes of an ultrasonic pulse sent out immediately beforehand have (sufficiently) died away and/or were received. A new ultrasonic pulse is furthermore preferably sent out only if the (significant) echoes of an ultrasonic pulse sent out immediately beforehand from a (predefined) measurement window or measurement range have (sufficiently) died away and/or were received.

According to an advantageous embodiment, it is proposed that a maximum pulse repetition rate of the pulsed Doppler measurement is less than two times a maximum occurring Doppler shift. The maximum pulse repetition rate of the pulsed Doppler measurements is preferably less than the maximum occurring or expected Doppler shift. If the maximum pulse repetition rate is less than twice the maximum occurring Doppler shift, the Nyquist sampling theorem is in principle violated. However, this violation may be necessary to perform a PWD method in a vascular support system.

According to an advantageous embodiment, it is proposed that the operating parameter is at least one rotational speed, one current, one power, or one pressure. The operating parameter is preferably a rotational speed (or rotation rate) of the flow machine, e.g., of a drive (e.g., of an electric motor) and/or of a paddle wheel of the flow machine. The at least one operating parameter furthermore preferably comprises a rotational speed of the flow machine and a differential pressure across the flow machine.

According to an advantageous embodiment, it is proposed that a plausible range in which plausible measurement results can be located is (a priori) determined using the operating parameter. In this context, a window function or windowing can be used in the frequency analysis (e.g., by means of discrete Fourier transformation) of the (reflected and then) received ultrasonic pulse. A so-called Hamming window is preferably used. The windowing, in particular the Hamming window, can advantageously be formed as a function of the operating parameter and/or the expected and/or estimated flow velocity (on the basis of the operating parameter) and/or the expected and/or estimated fluid volume flow (on the basis of the operating parameter).

According to an advantageous embodiment, it is proposed that a fluid volume flow through the support system is determined using the flow velocity. In other words, this relates in particular to a fluid volume flow which flows (only) through the support system itself, e.g., through an (inlet) tube or an (inlet) cannula of the support system. The fluid volume flow is usually the so-called pump volume flow ($Q_p$), which only quantifies the flow through the support system itself. If this value is known in addition to the total volume flow or heart-time volume (QHZV), the so-called level of support can be calculated from the ratio of $Q_p$ to $Q_{HZV}$ (i.e., $Q_p/Q_{HZV}$). In order to determine the fluid volume flow, the determined flow velocity can be multiplied, for example, with a flow cross section of the support system, in particular a tube or cannula flow cross section.

According to a further aspect, an implantable, vascular support system is, comprising:
 an ultrasonic sensor configured to carry out a pulsed Doppler measurement,
 a flow machine,
 a processing unit configured to correct a possible ambiguity of a measurement result of the ultrasonic sensor using the operating parameter of the flow machine.

The support system is preferably a left ventricular heart support system (LVAD) or a percutaneous, minimally invasive left-heart support system. Furthermore, the support system is preferably fully implantable. In other words, this means in particular that the means required for the detection, in particular the ultrasonic sensor, are completely located in the body of the patient and remain there. The support system can also be designed in multiple parts or with several components that can be arranged at a distance from one another, so that, for example, the ultrasonic sensor and the processing unit (measuring unit) can be separated from one another by a cable. In the multi-part design, the processing unit arranged separately from the ultrasonic sensor can also be implanted or arranged outside the body of the patient. In any case, it is not absolutely necessary for the processing unit to also be arranged in the body of the patient. For example, the support system can be implanted such that the processing unit is arranged on the skin of the patient or outside the body of the patient and a connection is established to the ultrasonic sensor arranged in the body. The support system is particularly preferably configured and/or suitable for being arranged at least partially in a ventricle, preferably in the left ventricle of a heart, and/or in an aorta, in particular in the aortic valve position.

The support system furthermore preferably comprises a tube (or a cannula), in particular an inlet tube or inlet cannula, a flow machine, such as a pump and/or an electric motor. The electric motor is regularly a component of the flow machine. The (inlet) tube or the (inlet) cannula is preferably configured such that in the implanted state, it can guide fluid from a (left) ventricle of a heart to the flow machine. The support system is preferably elongated and/or tubular. The tube (or the cannula) and the flow machine are preferably arranged in the region of opposite ends of the support system.

In particular, precisely or only one ultrasonic sensor is provided. The ultrasonic sensor preferably comprises precisely or only one ultrasound transducer element. This is in particular sufficient for a Doppler measurement if the PWD method is used.

The flow machine is preferably designed at least in the manner of a pump or an (axial or radial) compressor. The flow machine can provide at least one of its (current) operating parameters of the processing unit. In addition, a control unit for controlling or regulating the flow machine can be provided, which, for example, controls or regulates at least one rotational speed or one power of the flow machine as a function of (among other things) a flow velocity determined by way of example by the processing unit.

The support system is preferably configured to carry out a method proposed here.

According to a further aspect, a use of an operating parameter of a flow machine of an implanted vascular support system for correcting a possible ambiguity of a measurement result of an ultrasonic sensor of the support system is proposed. Preferably, at least one method proposed here or a support system proposed here is used for correcting a possible ambiguity of a measurement result of an ultrasonic sensor.

The details, features, and advantageous embodiments discussed in connection with the method can also arise accordingly in the support system presented here and/or in the use and vice versa. In this respect, reference is made in full to the explanations there regarding the detailed characterization of the features.

The solution presented here as well as its technical environment are explained in more detail below with reference to the figures. It should be pointed out that the invention is not to be limited by the exemplary embodiments shown. In particular, unless explicitly stated otherwise, it is also possible to extract partial aspects of the facts explained in the figures and to combine them with other components and/or insights from other figures and/or the present description. The following are shown schematically:

DETAILED DESCRIPTION

The vascular support system is preferably a ventricular and/or cardiac support system or a heart support system. Two particularly advantageous forms of heart support systems are systems positioned in the aorta according to FIG. 2 and systems positioned apically according to FIG. 4. The respective systems are explained in more detail in connection with FIG. 1 (aortic) and FIG. 3 (apical).

Figure 1:
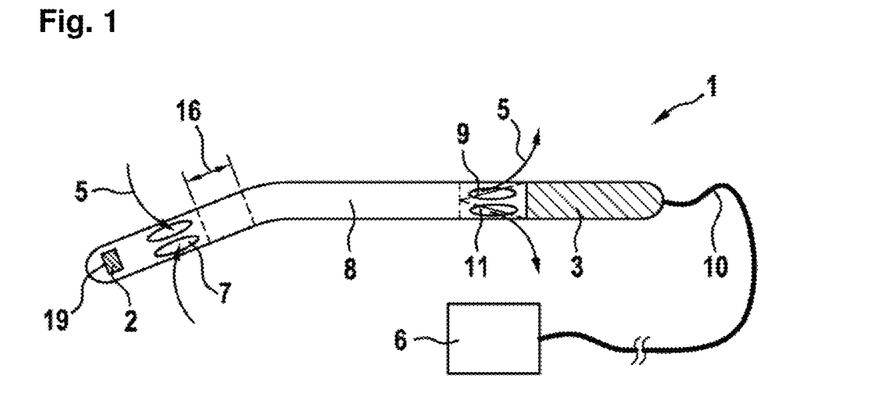
FIG. 1 an implantable vascular support system.

FIG. 1 schematically shows an implantable vascular support system 1. FIG. 1 illustrates an embodiment of an aortically positioned (cf. FIG. 2) or positionable support system 1. The support system 1 comprises an ultrasonic sensor 2 configured to carry out a pulsed Doppler measurement, a flow machine 3, and a processing unit 6 configured to correct a possible ambiguity of a measurement result of the ultrasonic sensor 2 using the operating parameter of the flow machine 3. The ultrasonic sensor 2 in this case comprises by way of example precisely one ultrasound (transducer) element 19.

In this case, the support system 1 according to FIG. 1 furthermore comprises, by way of example, a distal part with inlet openings 7 through which the blood can be drawn into the interior of the system, and an inlet tube 8 (which is formed in the manner of an inlet cannula in the aortic embodiment according to FIG. 1). In addition, the flow machine 3 is equipped by way of example with an impeller 9. In this case, a supply cable 10 is positioned by way of example proximally to the drive (e.g., electric motor; not shown here) of the flow machine 3. In the region of the impeller 9, there are also outlet openings 11, through which the blood can be discharged. During operation, a fluid volume flow 5 flows through the inlet tube 8, said fluid volume flow entering the support system 1 via the inlet openings 7 and exiting again via the outlet openings 11. This fluid volume flow 5 can also be referred to as a so-called pump volume flow.

Figure 2:
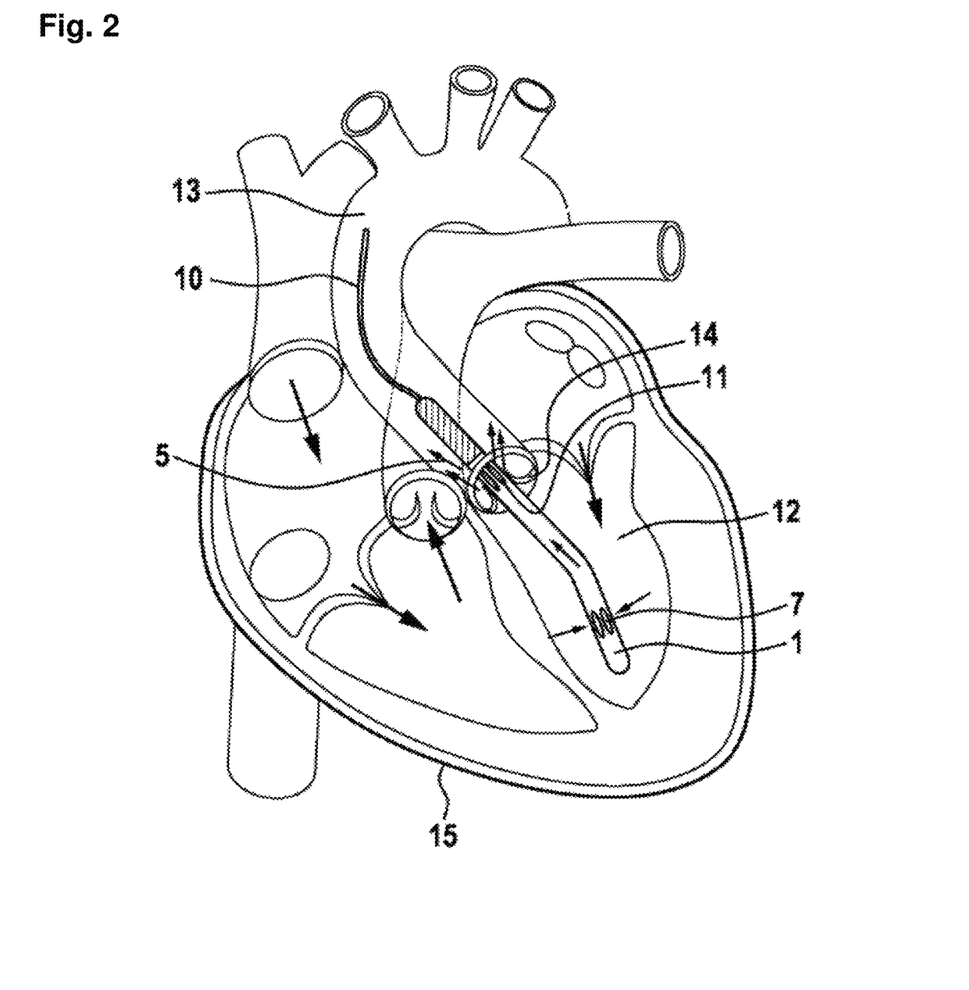
FIG. 2 the support system according to FIG. 1 implanted in a heart.

FIG. 2 schematically shows the support system 1 according to FIG. 1 implanted in a heart 15. The reference signs are used uniformly so that reference can be made to the above explanations.

The inlet openings 7 are located in the implanted state, for example, in the region of the ventricle 12, while the outlet openings are located in the implanted state in the region of the aorta 13. This orientation of the support system 1 is merely exemplary here and not mandatory; rather, the support system can be oriented in the reverse direction, for example. In this case, the system is furthermore implanted by way of example in such a way that it passes through the aortic valve 14. Such an arrangement can also be referred to as a so-called aortic valve position.

Figure 3:
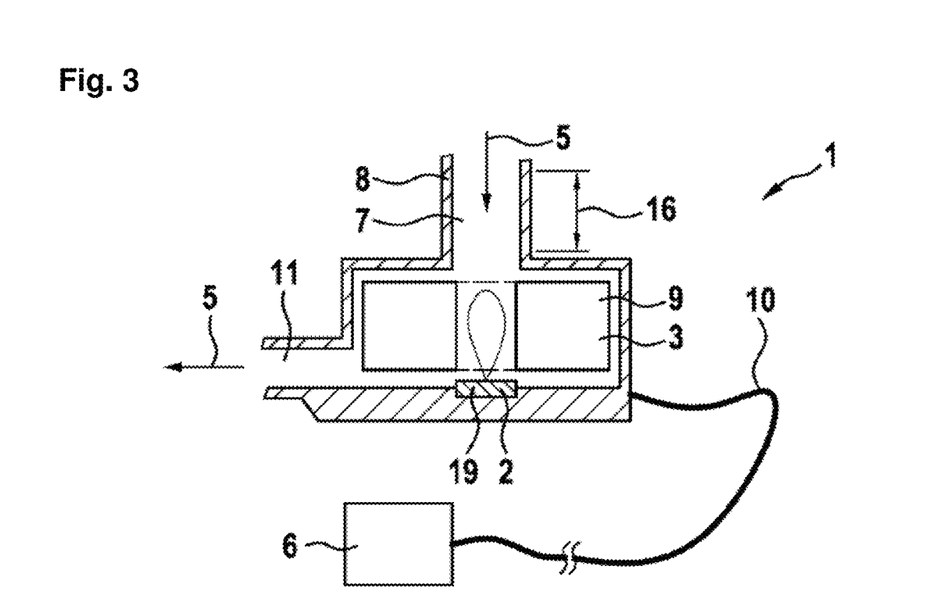
FIG. 3 a further implantable vascular support system.

FIG. 3 schematically shows a further implantable vascular support system 1. FIG. 3 illustrates an embodiment of an apically positioned (cf. FIG. 4) or positionable support system 1. The functioning of an apically implanted system is in principle comparable so that uniform reference signs can be used for all components in this case. Reference is therefore made here to the above explanations regarding FIG. 1.

Figure 4:
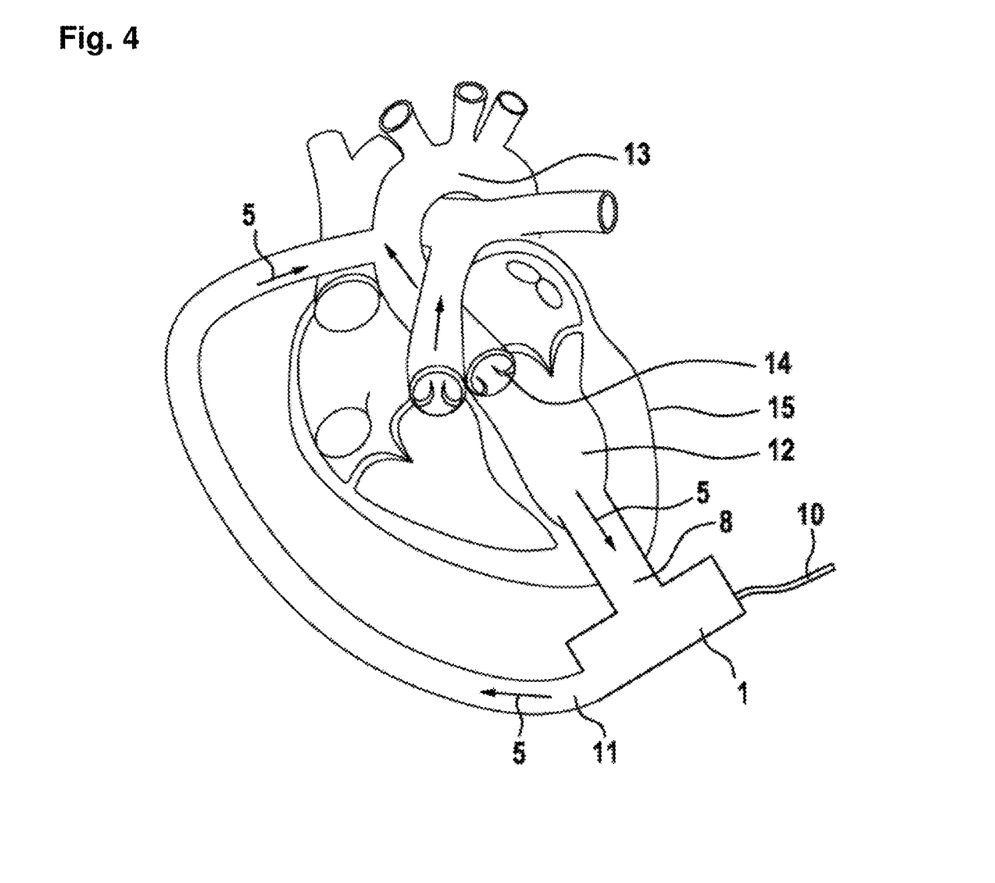
FIG. 4 the support system according to FIG. 3 implanted in a heart.

FIG. 4 schematically shows the support system 1 according to FIG. 3 implanted in a heart 15. The reference signs are used uniformly so that reference can also be made here to the above explanations.

Figure 5:
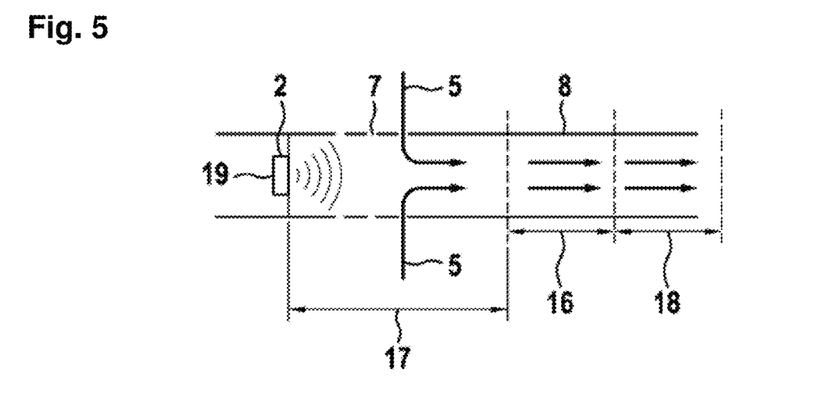
FIG. 5 an exemplary illustration of a Doppler measurement.

FIG. 5 schematically shows an exemplary illustration of a Doppler measurement. For this purpose, the ultrasonic sensor 2 of the support system 1 according to FIG. 1 is used by way of example in order to carry out a measurement in an inlet tube 8 of the support system 1 according to FIG. 1.

The measurement window, also referred to as the observation window and/or measurement range, for the ultrasound measurement is marked in FIGS. 1, 3, and 5 with reference sign 16. The selection of the measurement window 16 depends on the specific design of the (heart) support system 1 and should in principle be positioned where suitable flow conditions prevail. For example, FIG. 5 shows a simplified sectional view of the distal end of the embodiment of FIG. 1. In this case, it is shown schematically that no parallel flow lines prevail to the left of the measurement window 16 in the range 17. Since the Doppler effect is also a function of the $\cos(\alpha)$ between the main beam direction of the ultrasound transducer and the main flow direction, it is advantageous to measure in a range of parallel flow lines. Although a measurement window (e.g., range 18) positioned too far away is possible in principle, it can intensify the aliasing effect explained below and/or provide strong attenuation of the ultrasound signal.

The ultrasonic sensor 2 is configured to carry out a pulsed Doppler measurement. The pulsed Doppler (pulsed wave Doppler; in short: PWD) method is basically used for ultrasound measurement in this case. The ultrasonic sensor 2 and the processing unit 6 can therefore also be referred to below as a so-called PWD system.

The measurement window 16 can typically be selected electronically in the PWD system so that a statement about the flow conditions in different regions of the flow guidance can also advantageously be made by means of measurement windows 16 of different depths.

In the (apical) embodiment according to FIG. 4, the blood flows toward the ultrasound element 19 in the opposite direction. The rotating impeller 9 is located between ultrasound element 19 and inlet tube 8. In this case, strong turbulence in the blood flow is to be expected so that it is also particularly advantageous here to position the measurement window 16 in front of the impeller 9, approximately in the region of the inlet tube 8.

The relatively high flow velocities in the range of the measurement window 16 in relation to the distance of the ultrasound (transducer) element 19 from the measurement window 16 have a great influence on the PWD application in both (heart) support system variants, predominantly in the (aortic) variant according to FIG. 1.

Figure 6:
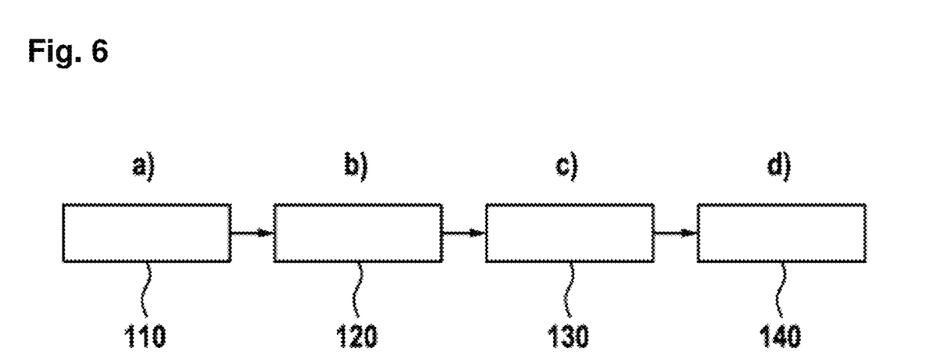
FIG. 6 a sequence of a method presented here in a normal operating procedure, FIG. 7 an exemplary Doppler frequency spectrum, FIG. 8 a further exemplary Doppler frequency spectrum, and FIG. 9 a functional illustration of a possible embodiment of the method presented here.

FIG. 6 schematically shows a sequence of a method presented here in a normal operating procedure. The method is used to determine at least a flow velocity or a fluid volume flow of a fluid flowing through an implanted vascular support system 1 (cf. FIGS. 1 to 5). The illustrated order of the method steps a), b), c), and d) with the blocks 110, 120, 130, and 140 is only exemplary. In block 110, a pulsed Doppler measurement is carried out by means of an ultrasonic sensor 2 of the support system 1. In block 120, a measurement result from step a) which has a possible ambiguity is evaluated. In block 130, at least one operating parameter of a flow machine 3 of the support system 1 is provided. In block 140, at least the flow velocity or the fluid volume flow is determined using the measurement result evaluated in step b). In the method, the possible ambiguity of the measurement result is corrected using the operating parameter.

For an exemplary illustration of the method, a system according to FIG. 1 with the following parameters is assumed:
inner diameter of the inlet tube: 5 mm
maximum blood flow to be measured: 9 liters/minute
resulting maximum flow velocity: 7.64 meters/second
sound speed in blood: 1540 m/s
frequency of ultrasound: 6 MHz
distance of the ultrasound transducer from the start of the measurement window: 25 mm
ultrasound oscillation cycles per sent-out ultrasonic PVD pulse: 10
resulting burst length (10 oscillations at 1540 m/s): 2.57 mm An ultrasonic pulse is sent out at the ultrasound element 19 and propagates in the direction of the measurement window 16. After sending out the pulse, the PWD system switches to the receiving direction and receives the portions that are continuously scattered back by scattering bodies in the blood, for example. The transit time of the pulse from the ultrasound element to the measurement window and from the measurement window back to the ultrasound element is taken into account in the process. In the case shown, the total relevant propagation path is thus 55.13 mm long (ultrasound element 19 to start of measurement window 16 plus burst length×2). The PWD system is switched back to transmission mode and the next pulse is sent out at the earliest when the last echo from the range of the measurement window 16 has arrived. In the specifically considered case, the pulse transit time limits the maximum pulse repetition rate to 27.93 kHz.

On the other hand, the maximum Doppler shift occurring in the case shown is 59.53 kHz. In a complex-value evaluation (10 demodulation), this leads to a minimum pulse repetition rate of 59.53 kHz, in which the present Doppler shift can be interpreted without ambiguity. However, since the measurement is carried out with a maximum of 27.93 kHz (maximum pulse repetition rate; see above), the Nyquist sampling theorem is violated in this case and ambiguities generally occur in the resulting Doppler spectrum. In this case, these ambiguities are resolved using an operating parameter of the flow machine of the support system in order to be able to make a clear statement about the main flow velocity in the observation window.

Figure 7:
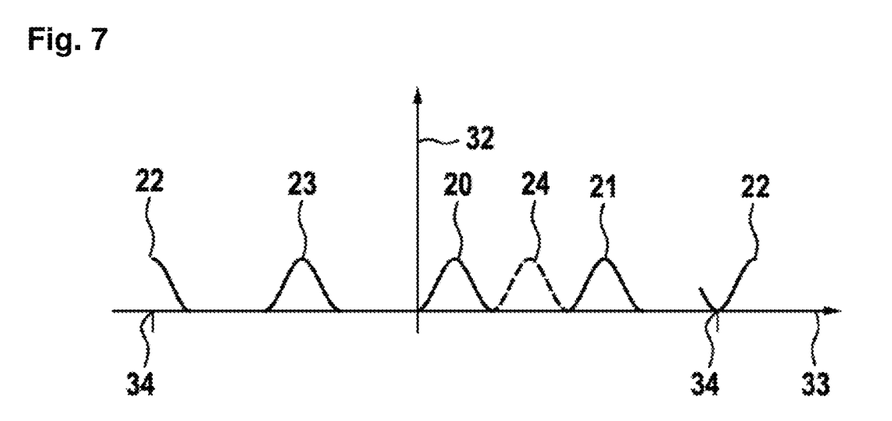
Figure 8:
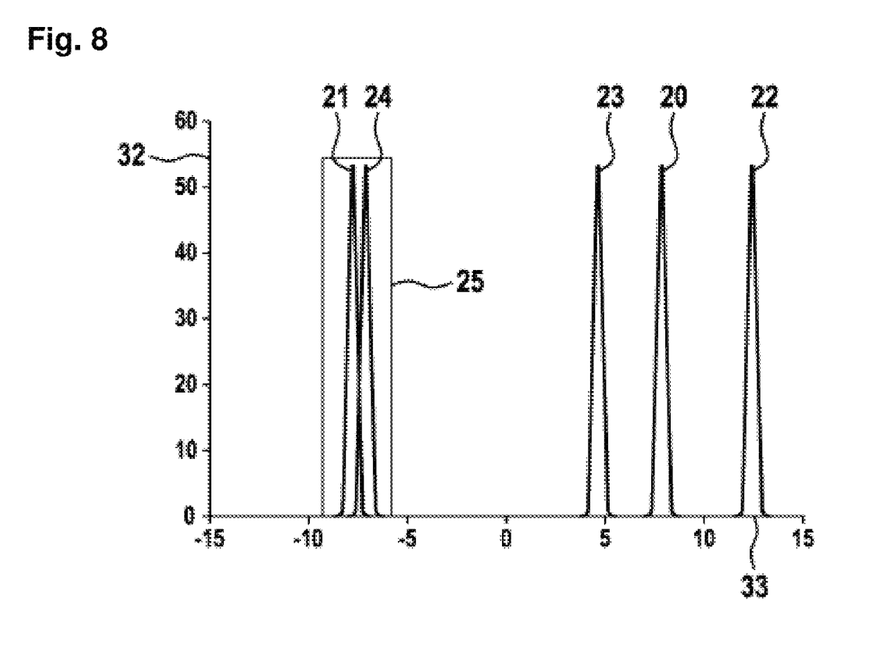

FIG. 7 schematically shows an exemplary Doppler frequency spectrum. Here, a schematic illustration of the previously presented relationships in the frequency spectrum is shown. A corresponding illustration of the shown relationships is also illustrated in FIG. 8.

FIG. 7 shows the amplitude 32 of the Doppler signal over the (averaged) frequency 33 with fixed pulse repetition rate 34 (PRF). The (fixed) pulse repetition rate 34 in the example considered here is 27 kHz. Simplified spectra for various flow velocities of the fluid (here: the blood) are shown in FIG. 7. A first flow velocity 20 is less than a second flow velocity 21, which in turn is less than a third flow velocity 22, which in turn is less than a fourth flow velocity 23, which in turn is less than a fifth flow velocity 24.

It can be seen that at the third flow velocity 22, there is already a violation of the Nyquist theorem, i.e., the Doppler frequency is in the range of the pulse repetition rate (PRF; here 27 kHz by way of example). With further increasing flow velocity of the blood, the spectrum moves from the negative frequency range to the coordinate origin. Here, there is already ambiguity about the direction of flow, i.e., either a fast flow toward the ultrasound element or a slower flow away from the ultrasound element. With further increasing flow velocity, the spectrum of the fifth flow velocity 24 appears in the ambiguity range of high or low flow velocity.

The solution presented here advantageously allows a resolution of such ambiguities. In principle, a comparatively rough range estimation can contribute to this purpose since the ultrasound method still works with high precision (resolution to 1-2 decimal places of the flow velocity in meters/second or of the volume flow in liters/minute), but ambiguity about the range of several meters/second or liters/minute is present.

FIG. 8 schematically shows another exemplary Doppler frequency spectrum. FIG. 8 illustrates the problem and the resolution of ambiguity once again using the example with the parameters used above $f_{us}$=6 MHz, PRF=27.93 kHz, $c_{blood}$=1540 m/s, and a windowing (window function) with a so-called Hamming window 25. The figure shows the frequency behavior at the following flow velocities:

first flow velocity 20=−1 m/s,
second flow velocity 21=+1 m/s,
third flow velocity 22=2 m/s,
fourth flow velocity 23=3 m/s,
fifth flow velocity 24=4.5 m/s.

In this context, a negative velocity means blood flowing toward the ultrasound element and appears in a frequency shift with a positive sign.

This example shows that the measured frequency peaks are very close to one another at flow velocities of 1 m/s and 4.5 m/s. This ambiguity can be resolved by the (a priori) knowledge of the approximate velocity on the basis of the operating parameter of the flow machine.

This approximate velocity interval $v_{int}$ (plausible range of the flow velocity) can be resolved with the aid of the following formula to a corresponding Doppler shift or a Doppler shift interval fd.int.

$$f_{d,int} = \frac{2 \cdot f_0}{c_{Blut}} \cdot v_{int}$$

In the example, the corresponding Doppler shift interval is 31.95 kHz to 35.84 kHz. In order to shift the corresponding frequency interval into the frequency range that can be represented with the PRF used, the determined non-representable frequencies can be converted into the representable frequency range using the following formula (for positive flow velocities).

$$f_{d,int,PRF} = (f_{d,int} \bmod PRF) - \frac{PRF}{2}$$

For the values shown in the example, the frequency interval that can be predicted by means of the operating parameter thus includes all frequencies between −9.95 kHz and −6.05 kHz. All frequencies measured in this interval correspond to velocities in the range of 4.1 m/s to 4.6 m/s.

The exact velocity (actual flow velocity) can be determined by a calculation from the number of spectral "wraps" with the aid of the operating parameter interval (frequency interval that can be predicted by means of the operating parameter) and successive back calculation from the measured frequency using the formulas already shown. A "wrap" here refers to the jump of a signal from the greatest positive representable frequency ($f_{pRF}/2$) to the representable negative frequency of highest magnitude ($-f_{pRF}/2$). The true frequency is determined according to the formula $$f_d = n f_{PRF} + f_{meas}$$

where the parameter n denotes the number of spectral "wraps." For low flow velocities, $f_d = f_{meas}$; at higher velocities, ambiguities occur with regard to the value of n, which can be resolved according to the solution proposed here by additional knowledge (the operating parameter(s) of the flow machine).

Figure 9:
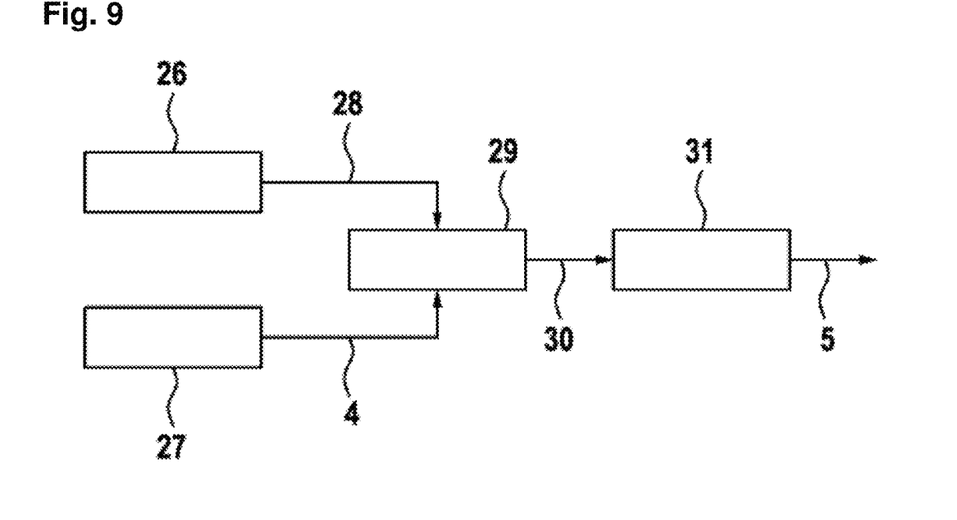

FIG. 9 schematically shows a functional illustration of a possible embodiment of the method presented here. The method in accordance with the illustration according to FIG. 9 serves to resolve the ambiguities. A PWD volume flow measurement 26 and a motor characteristic map-based volume flow measurement 27 take place in parallel or sequentially. The PWD volume flow measurement 26 can, for example, be carried out during step a). The motor characteristic map-based volume flow measurement 27 can be carried out, for example, between steps c) and d) or during step d). The PWD volume flow measurement 26 provides a Doppler spectrum 28. This can occur during step b), for example. The motor characteristic map-based volume flow measurement 27 provides an estimated (rough) fluid volume flow 4. This can occur, for example, between steps c) and d) or during step d). The Doppler spectrum 28 and the estimated fluid volume flow 4 are sent to an anti-aliasing unit 29. The anti-aliasing unit 29 determines from the estimated fluid volume flow 4 the (plausible) range in which the (actual) flow velocity is located, and from the Doppler spectrum 28 and the (plausible) volume flow range the corrected flow velocity 30, which is here also referred to as (actual) flow velocity through the support system. The anti-aliasing unit 29 can, for example, be a component of the processing unit also described here. A volume flow calculation unit 31 combines the known cross-sectional geometry and the known flow profiles determined in a construction type-specific and flow velocity-dependent manner for the (actual) fluid volume flow 5.

The PWD volume flow measurement 26 can comprise the following steps:
sending out an ultrasonic pulse,
waiting until the relevant echo of the measurement window,
receiving the echo of the measurement window,
possibly waiting for another waiting period until distant echoes die away,
sending out the next ultrasonic pulse.

The generated data can be stored temporarily in a memory for later evaluation or (e.g., with parallel implementation in programmable logic) can be further processed directly. While the ultrasonic pulse from the desired measurement window arrives (time limitation), the received echo sequence with the known ultrasonic pulse frequency is generally demodulated ("downmixing into the baseband"). Subsequently, the obtained baseband signal is generally transformed into the frequency range (transformation from time to frequency range for calculating the Doppler spectrum).

The motor characteristic map-based volume flow measurement 27 (rough volume flow measurement) can comprise the following steps:
determining a pump operating parameter, such as rotation rate (revolutions per minute, in short: RPM), power consumption, current consumption, and/or pressure difference across the flow machine (e.g., pump), calculating the estimated fluid volume flow via a relationship determined in a type-specific manner or via interpolation (e.g., table-based interpolation) from a motor characteristic map determined in a type-specific manner.

The volume flow calculation unit 31, for example, carries out the following: multiplication of the known cross section in the range of the observation window 16 (formula symbol: A) with the flow velocity 30 (formula symbol: v), and a flow velocity-dependent flow profile correction parameter (formula symbol f(v)). In this case, the (actual) fluid volume flow (formula symbol $Q_p$) can result according to the following formula:

$$Q_p = f(v) \times v \times A$$

The anti-aliasing unit 29 and the volume flow calculation unit 31 can also be combined into one unit. In addition, the Doppler spectrum can be mapped directly to the volume flow $Q_p$, for example.

The solution presented here allows in particular one or more of the following advantages:
  highly accurate calculation of the pump volume flow by means of a Doppler ultrasonic sensor.
  combination of a high-precision Doppler ultrasound measurement and a rough estimation on the basis of motor operating parameters (e.g., one or more of rotational speed, current, power, built-up pressure) allows the operation of the ultrasound measurement with violation of the Nyquist theorem (necessity arising from geometric conditions) and a subsequent resolution of arisen ambiguities with the aid of the rough estimate.

The invention claimed is:

1. A method for determining a flow velocity of blood flowing through a cardiac support system, the method comprising:
  carrying out a pulsed Doppler measurement of blood flowing through the cardiac support system using an ultrasonic sensor of the cardiac support system to determine a measurement result, the cardiac support system further comprising:
    a flow machine; and
    a processing unit configured to correct a possible ambiguity of the measurement result of the ultrasonic sensor based on at least one operating parameter of the flow machine to determine at least the blood flow velocity or the blood volume flow;
  evaluating the measurement result to generate an evaluated measurement result, wherein the measurement result comprises the possible ambiguity;
  determining the at least one operating parameter of the flow machine of the cardiac support system;
  determining the blood flow velocity or the blood volume flow based on the evaluated measurement result; and
  correcting the possible ambiguity of the measurement result using the at least one operating parameter.

2. The method of claim 1, wherein carrying out the pulse Doppler measurement comprises emitting a second ultrasonic pulse after an echo of a prior first ultrasonic pulse has died away.

3. The method of claim 1, wherein evaluating the measurement result comprises determining that the pulsed Doppler measurement has a pulse repetition rate of less than two times a maximum Doppler frequency shift of the blood flowing through the cardiac support system.

4. The method of claim 1, wherein the at least one operating parameter is based on at least one of the following: a rotational speed of a drive of the flow machine, an electrical current of the flow machine, an electrical power of the flow machine, and a differential pressure across the flow machine.

5. The method of claim 4, wherein determining the flow velocity is further based on the at least one operating parameter.

6. The method of claim 1, further comprising determining a plausible range in which plausible measurement results can be located based on the at least one operating parameter.

7. The method of claim 1, further comprising determining a fluid volume flow of the blood flowing through the cardiac support system based on the flow velocity.

8. The method of claim 1, wherein the at least one possible ambiguity comprises several possible flow velocities of the flowing blood.

9. A cardiac support system comprising:
  a flow machine;
  an ultrasonic sensor configured to carry out a pulsed Doppler measurement of blood flowing through the cardiac support system; and
  a processing unit configured to correct a possible ambiguity of a measurement result of the ultrasonic sensor based on at least one operating parameter of the flow machine to determine at least the blood flow velocity or the blood volume flow.

10. The support system of claim 9, wherein, to correct the possible ambiguity, the processing unit is further configured to:
  cause the ultrasonic sensor to carry out a pulsed Doppler measurement using an ultrasonic sensor of the cardiac support system to determine the measurement result;
  determine the at least one operating parameter of the flow machine of the cardiac support system; and
  determine at least the blood flow velocity or the blood volume flow based on the measurement result, wherein the possible ambiguity of the measurement result is corrected using the operating parameter.

11. The cardiac support system of claim 9, wherein the ultrasonic sensor is further configured to carry out the pulsed Doppler measurement by emitting a new ultrasonic pulse only if an echo of an ultrasonic pulse sent out immediately beforehand has died away.

12. The cardiac support system of claim 9, wherein the measurement result comprises the possible ambiguity based on the pulsed Doppler measurement having a maximum pulse repetition rate of less than two times a maximum occurring Doppler shift of the flowing blood.

13. The cardiac support system of claim 9, wherein the at least one operating parameter comprises at least one of the following: a rotational speed of a drive of the flow machine, an electrical current consumption of the flow machine, an electrical power consumption of the flow machine, and a differential pressure across the flow machine, a derived parameter of the rotational speed of a drive of the flow machine, a derived parameter of the electrical current consumption of the flow machine, a derived parameter of the electrical power consumption of the flow machine, and a derived parameter of the differential pressure across the flow machine.

14. The cardiac support system of claim 13, wherein to determining at least the flow velocity or the fluid volume flow is further based on the at least one operating parameter.

15. The cardiac support system of claim 9, wherein to determine at least the blood flow velocity or the blood volume flow, the processing unit is configured to determine a plausible range in which plausible measurement results can be located based on the at least one operating parameter.

16. The cardiac support system of claim 9, wherein the blood volume flow through the cardiac support system is determined based on the blood flow velocity.

\* \* \* \* \*